United States Patent [19]

Tsouderos et al.

[11] Patent Number: 5,856,356

[45] Date of Patent: Jan. 5, 1999

[54] USE OF STRONTIUM SALTS AND PHARMACEUTICAL COMPOSITIONS THEREOF FOR THE TREATMENT OF ARTHROSIS

[75] Inventors: Yannis Tsouderos, La Celle Saint Cloud; Pascale Deloffre, Courbevoie; Michel Wierzbicki, L'Etang la Ville, all of France

[73] Assignee: Adir et Compagnie, Courbevoie, France

[21] Appl. No.: 873,117

[22] Filed: Jun. 11, 1997

[30] Foreign Application Priority Data

Jun. 17, 1996 [FR] France ................................. 96 07475

[51] Int. Cl.⁶ .................................................. A61K 31/28
[52] U.S. Cl. ............................................................ 514/492
[58] Field of Search ............................ 514/492; 424/600, 424/665

[56] References Cited

U.S. PATENT DOCUMENTS

| 4,152,431 | 5/1979 | Klein ........................................ 424/245 |
| 4,939,164 | 7/1990 | Wierzbicki et al. ..................... 514/423 |
| 5,128,367 | 7/1992 | Wierzbicki et al. ..................... 514/447 |

OTHER PUBLICATIONS

W.P. Saunders, "Dorland's Illustrated Medical Dictionary" 27th Edition, pp. 147, 148, 1197, and 1200 (1988).

*Primary Examiner*—Kevin E. Weddington
*Attorney, Agent, or Firm*—The Firm of Gordon W. Hueschen

[57] ABSTRACT

The invention relates to the use of strontium salts and pharmaceutical compositions thereof for the treatment of arthrosis through stimulation of the synthesis of proteoglycans and type II collagen by chondrocytes.

4 Claims, No Drawings

USE OF STRONTIUM SALTS AND PHARMACEUTICAL COMPOSITIONS THEREOF FOR THE TREATMENT OF ARTHROSIS

The present invention relates to the use of strontium salts for the production of pharmaceutical compositions intended for the prevention and treatment of arthrosis.

BACKGROUND OF THE INVENTION

The use of strontium salts for therapeutic purposes has already been the subject of numerous publications and patents. By way of example, U.S. Pat. No. 4,152,431 describes alkali metal salts which can be used in the treatment of inflammation. Patent WO-A-94/09798 presents sulfate complexes of various metals which are active in the treatment of skin diseases. The work by Olle Svensson et al. (*Acta Path. Microbiol. Immunol. Scand.*, Sect. A, 93, (1985), 115–120) shows that strontium plays a role in certain cases of rickets.

DESCRIPTION OF INVENTION

The applicant has now discovered that strontium, in the form of inorganic or organic salts, has remarkable pharmacological properties and finds application in therapy which is completely beneficial in the prevention and treatment of arthrosis.

Indeed, it has been discovered that strontium salts stimulate the synthesis, by human chondrocytes, of proteoglycans and of type II collagen.

These molecules are the two major components of the extracellular cartilaginous matrix. It is the combination of a high concentration of proteoglycans encrusted in a fibrous collagen network which confers on the tissue its mechanical properties.

Since the synthesis and the secretion of proteoglycans decrease with age, strontium salts are therefore of great interest in the prevention and treatment of arthrosis. Strontium salts are therefore particularly effective during the repair process which occurs in the initial phase of the disease.

The present invention relates to the use of divalent strontium salts of organic or inorganic acids for the production of pharmaceutical compositions intended for the prevention and treatment of arthrosis.

Among the inorganic acids used to salify strontium in order to obtain the salts according to the present invention, there may be mentioned more particularly hydrochloric, sulfuric, nitric, carbonic and phosphoric acids.

Among the organic acids used to salify strontium in order to obtain the salts according to the present invention, there may be mentioned more particularly tartaric, malic, maleic, malonic, fumaric, gluconic, oxalic, lactic, succinic, methanesulfonic, ethanesulfonic, camphoric and citric acids as well as 2-[N,N-di(carboxymethyl)amino]-3-cyano-4-carboxymethylthiophene-5-carboxylic acid.

By way of example and with no limitation being implied, the present invention relates to the use, according to the invention, of the following strontium salts:

1) distrontium salt of 2-[N,N-di(carboxymethyl)amino]-3-cyano-4-carboxymethylthiophene-5-carboxylic acid,
2) strontium citrate,
3) strontium camphorate,
4) strontium ethanesulfonate,
5) strontium methanesulfonate,
6) strontium succinate,
7) strontium lactate,
8) strontium oxalate,
9) strontium gluconate,
10) strontium fumarate,
11) strontium malonate,
12) strontium maleate,
13) strontium malate,
14) strontium tartrate,
15) strontium phosphate,
16) strontium carbonate,
17) strontium nitrate,
18) strontium sulfate,
19) strontium chloride.

The preferred strontium salt of the present invention is the distrontium salt of 2-[N,N-di(carboxymethyl)amino]-3-cyano-4-carboxymethylthiophene-5-carboxylic acid which has been described in patent EP-B-0 415 850 for its antiosteoporotic properties and its use in the treatment of skin and vascular ageing, of hepatic conditions and of dental conditions.

Arthrosis is anatomically characterized by an initial and primary destruction of the articular cartilages.

Under normal conditions, the renewal of the cartilage is a very slow process consisting of a phase of resorption by the chondrocytes which is directly compensated by a phase of formation by these same chondrocytes.

Under pathological conditions, the renewal of the cartilage may accelerate, leading to an early cartilage repair reaction followed by a cellular decompensation and a degradation of the cartilage. The repair reaction results from a clonal multiplication of the chondrocytes and from their increased synthesis of the matrix components of cartilage (D. Hamerman et al., *N. Eng. J. Med.*, (1989), 320 (20), 1322–1330).

This homeostatic reaction is not appropriate and depends on systemic hormones and growth factors the secretions of which decrease with age. The resorption of the cartilage is regulated by enzymes and free radicals produced by adjacent tissues, but also and especially by the chondrocyte itself.

It is therefore most particularly advantageous to have pharmaceutical compositions which make it possible to act on the chondrocytic metabolism, both on chondroformation and on chondroresorption.

These pharmaceutical compositions will be provided in forms suitable for administrations by the oral, parenteral, transcutaneous, nasal, rectal or perlingual route, and especially in the form of injectable solutions, tablets, sublingual tablets, glossettes, gelatin capsules, capsules, lozenges, suppositories, creams, ointments, skin gels and the like.

In addition to a strontium salt, the pharmaceutical compositions according to the invention contain one or more excipients or vehicles chosen from diluents, lubricants, binders, disintegrating agents, absorbents, colorants, sweeteners and the like.

By way of example and with no limitation being implied, there may be mentioned:

for the diluents: lactose, dextrose, sucrose, mannitol, sorbitol, cellulose, glycerin, for the lubricants: silica, talc, stearic acid and its magnesium and calcium salts, polyethyleneglycol, for the binders: aluminum and magnesium silicate, starch, gelatin, tragacanth, methyl-cellulose, sodium carboxymethylcellulose and polyvinylpyrrolidone, for the disintegrants: agar, alginic acid and its sodium salt, effervescent mixtures.

The useful dosage varies according to the patient's sex, age and weight, the route of administration, the nature of the condition and the treatments which may be associated, and is between 25 mg and 3 g of strontium per 24 hours, for example between 100 mg and 2 g of strontium per 24 hours.

The following examples illustrate the invention without, however, limiting it in any way.

PHARMACOLOGICAL STUDY

Example A

Studies of the Effects of the Strontium Salts According to the Invention on the Metabolism of the Chondrocytes A) Procedure a) Culture of Human Chondrocytes The chondrocytes are cultured for a period of short duration in order to preserve their pheno-type. In this method, the cartilage is removed from the knees of human corpses immediately after death. An excision of the superficial and median layers is performed, avoiding the calcified layer. The cartilage is cut into small pieces and then subjected to enzymatic digestion. The cartilage fragments are then successively treated with hyaluronidase, pronase and collagenase. First, the cartilage pieces are incubated with the hyaluronidase, previously dissolved in Dulbecco's Modified Eagle's Medium (DMEM, ICN Biomedical) (0.5 mg/ml; 3 g of cartilage per 10 ml of enzymatic solution), for 30 minutes at 37° C. and with constant stirring (200 revolutions per minute).

Secondly, the cartilage fragments are placed in a pronase solution (1 mg/ml in DMEM; 3 g of cartilage per 10 ml of enzymatic solution) and incubated with this enzyme for one hour at 37° C.

The cartilage fragments are then incubated with collagenase 51 mg/ml; 3 g per 10 ml of enzymatic solution) dissolved in DMEM containing 1% Ultrosser G (serum substitute from Gibco, Gand, Belgium), for 20 hours at 37° C. and with constant stirring (200 revolutions per minute). The cells are filtered on nylon tulle (pore diameter: 25 $\mu$m), washed 3 times, counted (number ranging from $1 \times 10^6$ to $5 \times 10^6$ cells/ml depending on the scope of the study) and then resuspended in an appropriate culture medium. The cells are thus maintained in suspension with constant stirring in a gyratory mixer (100 revolutions per minute) and under an atmosphere composed of 95% air and 5% carbon dioxide gas. The cells and the supernatant are separated by centrifugation (1000 revolutions per minute for 5 minutes). The cell aggregates and the supernatant are stored at –20° C.

b) Treatments of the chondrocytic cultures

The chondrocytes ($\pm 1.5 \times 10^6$ cells/ml) are cultured for 24, 48 and 72 hours in the absence or in the presence of a strontium salt to be tested, at the concentrations of $10^{-4}$M, $5 \times 10^{-4}$M and $10^{-3}$M. For each concentration of compound to be tested and for the corresponding controls, a batch of three culture flasks was used. Each flask contains ±1 to $1.5 \times 10^6$ chondrocytes. The experiment was repeated twice on two different donors. The proteoglycans and the collagen II are measured in the supernatants and in the cellular phases.

c) Parameters studied

1. Chondroformation Parameters

The cultures are performed in DMEM supplemented with 1% ITS+ and ascorbate at 50 $\mu$g/ml. ITS+ contains: 6.25 $\mu$g/ml of insulin, 625 $\mu$g/ml of transferrin, 6.25 $\mu$g/ml of selenium, 1.25 mg/ml of bovine serum albumin and 535 $\mu$g of linoleic acid. The proteoglycans and the type II collagen are directly assayed in the supernatant previously supplemented with protease inhibitors. Before the measurements, the cell aggregates are homogenized by ultrasonic dissociation (3 pulses of 10 seconds) in PBS (phosphate buffered saline) containing the protease inhibitors. The protease inhibitors used in this study are 6-aminohexanoic acid (0.1M), benzamidine hydrochloride (0.05M), a trypsin inhibitor ($5 \times 10^{-8}$M), EDTA (0.01M) and sodium nitride ($6.7 \times 10^{-3}$M).

*Radioimmunological assay, (RIA) of the proteoglycans

The proteoglycans released into the culture medium (CM) and present in the chondrocytic aggregates (CA) are assayed according to the method described by P. Gysen and P. Franchimont (J. Immunoassay, (1984), 5, 221–243). The analytical sensitivity of RIA is 0.6 ng/tube.

The intra- and inter-assay coefficients of variation are less than 10 and 20% respectively, along the linear portion of the curve. The antibodies are directed solely against the antigenic determinant of the protein core. The sum of the proteoglycans in the CM and in the CA corresponds to the total production of the molecule.

*Synthesis of sulfated glycomnoglycans

This method evaluates the production of sulfated proteoglycans by incorporation of $^{35}SO_4$. The chondrocytes treated with strontium salts are cultured in the presence of $Na_2{}^{35}SO_4$ for 24 hours. The cells are separated by centrifugation and rinsed. The glycoseaminoglycans present in the culture medium and the cells are extracted in the presence of protease inhibitors. The total production of sulfated glycoseaminoglycans during the 24 hours of culture is evaluated by counting the radioactivity. The extracts are subjected to chromatography on Sepharose CL 2B (agarose-dextran chromatography matrix from Pharmacia Biotech) in order to study their physicochemical structure.

*Radioimmunological assay (RIA) of the type II collagen

The type II collagen released into the culture medium and present in the cellular phase is assayed according to the RIA method described by Y. Henrotin et al. (J. Immunoassay, (1990), 11, 555–578). The detection limit for the assay is 3 ng/tube. The intra- and inter-assay coefficients of variation are 8 and 15% respectively. The antibodies are directed against the helical part of the native molecule.

2. Chondroresorption Parameters

The cultures are performed in DMEM supplemented with 1% TS+ and ascorbate at 50 $\mu$g/ml. TS+ contains: 625 $\mu$g/ml of transferrin, 6.25 $\mu$g/ml of selenium, 1.25 mg/ml of bovine serum albumin and 535 $\mu$g of linoleic acid. The proteoglycans and the type II collagen are directly assayed in the supernatant previously supplemented with protease inhibitors. Before the measurements, the cell aggregates are homogenized by ultrasonic dissociation (3 pulses of 10 seconds) in PBS containing protease inhibitors.

*Assay of the Stromelysine Activity

The case in degradation activity is assayed using the labeled resorufin-case in obtained from cows' milk (Boehringer Mannheim). In this study, the activation of latent stromelysine is produced by addition of APMA (para-aminophenylmercuric acetate), Sigma Chemie, Deinsenhofen, Germany) at the final concentration of 2 mM. The conditioned medium of chondrocytes is incubated for 4 hours at 37° C. The activated culture medium is incubated with 20 μg of labeled resorufin-casein for 18 hours at 37° C. in a titrated buffer solution (0.2M Tris-HCl; pH 7.8) containing 0.02M calcium chloride. After this incubation, the enzymatic reaction is stopped by addition of trichloroacetic acid at the final concentration of 1.6%. The sample is centrifuged at 7000 g for 15 minutes. Under these conditions, the uncleaved casein is completely precipitated, whereas more than 95% of the cleaved casein remains in the supernatant. The measurements are performed by fluorescence. The excitation wavelength is 574 nm and the emission wavelength is 584 nm.

The standard curve is obtained by incubating increasing quantities of purified stromelysine. In parallel, samples containing 10 mM EDTA added before the incubation are treated in a similar manner, providing control values which are subtracted from the values obtained with the active medium. The control values never exceed 5% of the fluorescence measured in the active medium. All the assays are carried out in duplicate.

B) Results

The results are expressed as ratios of proteoglycans and type II collagen released into the culture media and present in the cellular phases, per μg of DNA. The mean values ± the standard deviations of the mean values are calculated. The comparisons between the groups are formed using the non-paired Student's t test; the differences are considered to be statistically significant when $p<0.05$.

1. Chondroformation parameters

*Radioinmmunological assay (RIA) of thee proteoglycans

The following results show the effects, at various concentrations, of the distrontium salt of 2-[N,N-di(carboxymethyl)amino]-3-cyano-4-carboxymethylthiophene-5-carboxylic acid on the total production (culture medium + cellular phase) of proteoglycans after 24, 48 and 72 hours of culture.

| Culture time | Concentration | ng/μg DNA* | Student's t test** |
|---|---|---|---|
| 24 hours | 0 (control) | 83.4 ± 4.1 | — |
| | $10^{-4}$M | 79.8 ± 3.5 | NS |
| | $5 \cdot 10^{-4}$M | 78.5 ± 3.4 | NS |
| | $10^{-3}$M | 89.7 ± 4.1 | NS |
| 48 hours | 0 (control) | 104 ± 7.65 | — |
| | $10^{-4}$M | 111 ± 15.4 | NS |
| | $5 \cdot 10^{-4}$M | 123 ± 3.6 | p < 0.05 |
| | $10^{-3}$M | 136 ± 13.8 | p < 0.05 |
| 72 hours | 0 (control) | 120 ± 8.5 | — |
| | $10^{-4}$M | 155 ± 2.51 | p < 0.05 |
| | $5 \cdot 10^{-4}$M | 173 ± 3 | p < 0.05 |
| | $10^{-3}$M | 176 ± 11.3 | p < 0.05 |

*mean ± standard deviation
**NS = not significant

*Production of sulfated glycoseaminoglycans

The results confirm, by a second method, the effects of the distrontium salt of 2-[N,N-di(carboxymethyl)amino]-3-cyano-4-carboxymethylthiophene-5-carboxylic acid (compound A) on the synthesis of proteoglycans and show that strontium chloride exhibits the same effects, which indicates that strontium is responsible for this stimulation of the chondroformation by the human chondrocytes.

The results obtained after 24 hours of culture are presented in the table below:

| Compound/concentration | c.p.m./$10^6$ cells | Student's t test |
|---|---|---|
| Control | 43 871 ± 1124 | — |
| Compound A/$10^{-3}$M | 52 005 ± 983 | p < 0.05 |
| $SrCl_2$/$2 10^{-3}$M | 52 839 ± 489 | p < 0.05 |

The chromatographic profiles obtained with the two strontium salts and in particular with the compound A show an increased synthesis of high-molecular weight glycoseaminoglycans. The table below presents the distribution (%) of the proteoglycans synthesized according to their molecular weight.

| | High molecular weight Kd < 0.13 | 0.13 < Kd < 0.7 | Low molecular weight Kd > 0.7 |
|---|---|---|---|
| Control | 27 | 42 | 30 |
| Compound A/$10^{-3}$M | 68 | 19 | 13 |
| $SrCl_2$/$2 \cdot 10^{-3}$M | 36 | 36 | 28 |

*Radioimmunological assay (RIA) of the type II collagen

The following results show the effects, at various concentrations, of the distrontium salt of the acid (compound A) on the production of the type II collagen released into the culture medium lo after 24, 48 and 72 hours of culture.

| Culture time | Concentration | ng/μg DNA* | Student's t test** |
|---|---|---|---|
| 24 hours | 0 (control) | 4.8 ± 0.2 | — |
| | $10^{-4}$M | 5 ± 0.2 | NS |
| | $5 \cdot 10^{-4}$M | 5.3 ± 0.3 | NS |
| | $10^{-3}$M | 5.1 ± 0.4 | NS |
| 48 hours | 0 (control) | 6.1 ± 0.5 | — |
| | $10^{-4}$M | 6.6 ± 0.3 | NS |
| | $5 \cdot 10^{-4}$M | 7.2 ± 0.5 | NS |
| | $10^{-3}$M | 8.6 ± 0.2 | p < 0.05 |
| 72 hours | 0 (control) | 6.4 ± 0.25 | — |
| | $10^{-4}$M | 5.9 ± 0.8 | NS |
| | $5 \cdot 10^{-4}$M | 7.4 ± 0.3 | p < 0.05 |
| | $10^{-3}$M | 8.8 ± 0.4 | p < 0.05 |

*mean ± standard deviation
**NS = not significant

2. Chondroresorption parameters

*Assay of the stromelysne ability

The following results show the effects, at various concentrations, of the distrontium salt of 2-[N,N-di(carboxymethyl)amino]-3-cyano-4-carboxymethylthiophene-5-carboxylic acid on the production of stromelysine after 24, 48 and 72 hours of culture.

| Culture time | Concentration | ng/μg DNA* | Student's t test** |
|---|---|---|---|
| 24 hours | 0 (control) | 0.69 ± 0.021 | — |
| | $10^{-4}$M | 0.73 ± 0.072 | NS |
| | $5 \cdot 10^{-4}$M | 0.72 ± 0.026 | NS |
| | $10^{-3}$M | 0.75 ± 0.026 | NS |
| 48 hours | 0 (control) | 1.43 ± 0.025 | — |
| | $10^{-4}$M | 1.45 ± 0.077 | NS |
| | $5 \cdot 10^{-4}$M | 1.48 ± 0.071 | NS |
| | $10^{-3}$M | 1.51 ± 0.010 | NS |
| | 0 (control) | 1.79 ± 0.065 | — |

-continued

| Culture time | Concentration | ng/μg DNA* | Student's t test** |
|---|---|---|---|
| 72 hours | $10^{-4}$M | 1.87 ± 0.025 | NS |
|  | $5 \cdot 10^{-4}$M | 1.78 ± 0.15 | NS |
|  | $10^{-3}$M | 2.05 ± 0.16 | $p < 0.05$ |

*mean ± standard deviation
**NS = not significant

Example B

Pharmaceutical Composition: Tablets

Tablets containing 500 mg doses of distrontium salt of 2-[N,N-di(carboxymethyl)an-ino]-3-Bass: cyano-4-carboxymethylthiophene-5-carboxylic acid, that is to say 170 mg of strontium.

| Preparation formula for 1000 tablets: | |
|---|---|
| Distrontium salt of 2-[N,N-di(carboxymethyl)amino]-3-cyano-4-carboxymethylthiophene-5-carboxylic acid | 500 g (that is to say 170 mg of strontium) |

-continued

| Preparation formula for 1000 tablets: | |
|---|---|
| Wheat starch | 1000 g |
| Lactose | 800 g |
| Magnesium stearate | 50 g |
| Silica | 20 g |
| Hydroxypropylcellulose | 50 g |

We claim:

1. A method for treating arthrosis in a living animal body comprising administering to the said living body an effective amount of a strontium salt.

2. The method of claim 1 wherein the strontium salt is the distrontium salt of 2-3-cyano-4-carboxymethylthiophene-5-carboxylic acid.

3. The method of claim 1 wherein the strontium salt is strontium chloride.

4. The method of claim 1 wherein the strontium salt is administered in the form of a pharmaceutical composition thereof in which it is present together with a pharmaceutically-acceptable excipient or vehicle.

* * * * *

UNITED STATES PATENT AND TRADEMARK OFFICE
CERTIFICATE OF CORRECTION

PATENT NO. : 5,856,356
DATED : Jan. 5, 1999
INVENTOR(S) : Y. Tsouderos, P. Deloffre, M. Wierzbicki It is certified that error appears in the above-identified patent and that said Letters Patent is hereby corrected as shown below:

Column 3, line 43: "51" should read -- (1 --.

Column 4, line 61: "case in" should read -- casein --.

Column 4, line 62: "case in" should read -- casein --.

Column 5, line 33: "thee" should read -- the --.

Column 6, line 29: Delete "lo" after the word "medium".

Column 6, line 50: "stromelysne" should read -- stromelysine --.

Column 7, line 15: "an-ino]-3-Bass: cyano-4-" should read -- amino]-3-cyano-4- --.

UNITED STATES PATENT AND TRADEMARK OFFICE
CERTIFICATE OF CORRECTION

PATENT NO. : 5,856,356
DATED : Jan. 5, 1999
INVENTOR(S) : Y. Tsouderos, P. Deloffre, M. Wierzbicki It is certified that error appears in the above-identified patent and that said Letters Patent is hereby corrected as shown below:

Column 8, line 15: Change "2-" to -- 2-[N,N-di(carboxymethyl)amino] --.

Signed and Sealed this

Sixth Day of April, 1999

Attest:

Q. TODD DICKINSON

*Attesting Officer*    *Acting Commissioner of Patents and Trademarks*